(12) United States Patent
Djeu et al.

(10) Patent No.: US 8,599,373 B1
(45) Date of Patent: Dec. 3, 2013

(54) MICROCAVITY RAMAN SENSOR AND METHOD OF USE

(75) Inventors: Nicholas Djeu, Tampa, FL (US); Andreas Muller, Tampa, FL (US)

(73) Assignee: University of South Florida, Tampa, FL (US)

( * ) Notice: Subject to any disclaimer, the term of this patent is extended or adjusted under 35 U.S.C. 154(b) by 21 days.

(21) Appl. No.: 13/542,282

(22) Filed: Jul. 5, 2012

Related U.S. Application Data

(60) Provisional application No. 61/505,270, filed on Jul. 7, 2011.

(51) Int. Cl.
*G01J 3/44* (2006.01)
(52) U.S. Cl.
USPC .......................................... 356/301; 356/300
(58) Field of Classification Search
USPC ........... 356/300, 301, 244, 36, 318, 417, 302, 356/308, 303, 311, 317
See application file for complete search history.

(56) References Cited

U.S. PATENT DOCUMENTS

| | | |
|---|---|---|
| 4,648,714 A | 3/1987 | Benner et al. |
| 4,784,486 A | 11/1988 | Van Wagenen et al. |
| 5,255,067 A | 10/1993 | Carrabba et al. |

OTHER PUBLICATIONS

Tobias J. Kippenberg, Sean M. Spillane, Bumki Min, and Kerry J. Vahala, Theoretical and Experimental Study of Stimulated and Cascaded Raman Scattering in Ultrahigh-Q Optical Microcavities, IEEE Journal of Selected Topics in Quantum Electronics, vol. 10, No. 5, Sep./Oct. 2004, pp. 1219-1228.
Xiaoyun Li, Yuxing Xia Li Zhan, and Juming Huang, Near-confocal cavity-enhanced Raman spectroscopy for multitrace-gas detection, Optics Letters, Sep. 15, 2008, vol. 33, No. 18, 2143-2145.
N. Linder, R Butendeich, C. Karnutsch, W. Schmid, S. Tautz, K. Streubel S. Rurlander, H. Schweizer, F. Scholz, 900 mW continuous wave operation of AlInGaP tapered lasers and superluminescent diodes at 640 nm, Lasers and Electro-Optics, 2004, pp. 900-901.

*Primary Examiner* — Tri T Ton
(74) *Attorney, Agent, or Firm* — Molly Sauter; Smith & Hopen, P.A.

(57) ABSTRACT

In accordance with the present invention, an ultra-sensitive Raman chemical sensor is provided that is based on an enhanced spontaneous emission as a result of cavity quantum electrodynamic effects. More specifically, the sensor in accordance with the present invention makes use of a double resonance of a microcavity with both the excitation laser frequency and the Raman frequency. As such, the Raman shift corresponds to an integer times the free spectral range of the microcavity. Because the Raman frequency directly depends on the excitation laser's frequency, the fulfillment of the resonance condition for the excitation laser frequency guarantees that resonance with the Raman frequency is also satisfied.

21 Claims, 2 Drawing Sheets

MICROCAVITY RAMAN SENSOR AND METHOD OF USE

CROSS-REFERENCE TO RELATED APPLICATIONS

The present invention claims priority to U.S. Provisional Patent Application No. 61/505,270, filed on Jul. 7, 2011 and entitled "Microcavity Raman Sensor and Method of Use".

BACKGROUND OF THE INVENTION

When a Raman active medium is placed in an optical cavity, a large enhancement in the scattering efficiency can be realized. The enhancement can be observed when the cavity is made resonant with either the wavelength of the excitation light or the wavelength of the Raman scattered light. The effect is maximized when the cavity is made simultaneously resonant with both, i.e., when a double resonance is obtained. The exact magnitude of the enhancement depends on, among other factors, the finesse of the cavity at the two wavelengths.

In the prior art the double resonance condition could be achieved only for a very thin solid sample with a thickness of less than one wavelength. The sample was made to have plane parallel surfaces, effectively creating a planar resonator with two flat partial reflectors forming the cavity. Because of the fixed spacing of the cavity, resonance with the wavelength of the excitation light could be established only for an off-axis laser beam. As a result, the resonance was accompanied by a high walk-off loss. Furthermore, planar resonators are inherently only quasi-stable, and are therefore precluded from having a high finesse even for axial beams because of diffraction. Finally, the extension of this approach to fluid samples is clearly not possible.

Accordingly, what is needed in the art is a microcavity arrangement capable of sustaining the double resonance condition with high finesse for Raman scattering in fluids.

SUMMARY OF THE INVENTION

In accordance with the present invention is provided a novel Raman sensor based on quantum electrodynamic effects capable of detecting trace amounts of chemicals in gases and liquids with a high degree of accuracy.

In accordance with an embodiment of the invention, an ultra-sensitive chemical sensor is provided that is based on an enhanced spontaneous Raman emission as a result of cavity quantum electrodynamic effects. More specifically, the sensor in accordance with the present invention makes use of a double resonance of a stable Fabry-Perot microcavity with both the excitation laser frequency and the Raman frequency. As such, the Raman shift corresponds to an integer times the free spectral range of the microcavity. Because the Raman frequency directly depends on the excitation laser's frequency, the fulfillment of the resonance condition for the excitation laser frequency guarantees that resonance with the Raman frequency is also satisfied.

In a particular embodiment, a Raman sensor for detecting the concentration of a species of interest in a sample may include a first substantially flat reflector and an adjustable optical fiber, wherein the adjustable optical fiber is translatable in a direction parallel to the fiber optic axis of the optical fiber, and a second substantially concave reflector positioned at a proximate end of the optical fiber and aligned substantially normally to the first reflector, the second reflector separated from the first reflector by a distance to form a microcavity having a microcavity length equal to the distance between the first reflector and the second reflector, wherein the microcavity length is dependent upon the Raman transition of a species of interest to be detected. The sensor may further include an excitation laser positioned to emit an excitation wavelength incident upon the first reflector and the second reflector, wherein the wavelength of the excitation laser is dependent upon the microcavity length between the first reflector and the second reflector and a Raman emission signal detector positioned to receive the Raman emission coupled out of the first reflector and to detect the concentration of the species of interest within a sample positioned between the first reflector and the second reflector.

To couple the laser beam into the microcavity, the present invention may include a dichroic filter positioned between the excitation laser and the first reflector, the dichroic filter having high reflectance at the wavelength of the excitation laser and high transmittance at the Raman emission wavelength.

To mode match the laser beam into the microcavity and to collimate the Raman emission coupled out of the first reflector onto the Raman emission signal detector, the present invention may include a lens positioned between the first reflector and the dichroic filter.

In a particular embodiment, the optical fiber may further be positioned within a close fitting ferrule to constrain the optical fiber and to allow translation of the optical fiber in the direction parallel to the fiber's optic axis.

The present invention may further include, an excitation light detector positioned at a distance from the distal end of the optical fiber to detect the transmitted laser power and a piezoelectric transducer coupled to a distal end of the optical fiber to adjust the length of the microcavity by translating the optical fiber in the direction parallel to the fiber's optic axis dependent upon the detected excitation laser power.

In operation, a sample containing a species of interest is introduced into a microcavity having a microcavity length dependent upon the Raman emission of the species of interest. An excitation laser signal having a wavelength determined by the microcavity length is then introduced into the microcavity. The Raman emission of the sample is then measured to determine the concentration of the species of interest within the sample.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

The ability of a cavity-resonant electric field to influence the spontaneous emission rate of an atomic transition is well known. In the case of Raman scattering, the rate of Raman photons spontaneously emitted into the cavity mode per molecule can be written as:

$$A_C = \frac{c^3 \nu_L \phi}{3\nu_R^3 V(\Delta\nu_C + \Delta\nu_R)} \frac{d\sigma}{d\Omega} \quad (1)$$

where $\nu_L$ and $\nu_R$ are the frequencies of the laser and Raman photons, $\phi$ is the laser photon flux density, V the cavity mode volume at the Raman wavelength, $\Delta\nu_c$ the cavity linewidth at the Raman wavelength, $\Delta\nu_R$ the Raman transition linewidth, and $d\sigma/d\Omega$ the differential Raman scattering cross section. If there are $\eta v$ molecules responsible for the Raman scattering in the mode volume, then the total rate of emission into the cavity mode can be found from:

$$\eta_V A_C = \frac{c^3 \nu_L N \phi}{3\nu_R^3 (\Delta\nu_C + \Delta\nu_R)} \frac{d\sigma}{d\Omega} \quad (2)$$

where N is the density of molecules of interest. The differential scattering cross section itself varies as the fourth power of the Raman shifted frequency, making the net emission rate into the cavity mode vary approximately as the square of $\nu_R$ for a fixed pump photon flux density.

Since the cavity mode in a stable Fabry-Perot resonator has an axially varying beam diameter, the photon flux density $\phi$ in Eqs. (1) and (2) is to be interpreted as an average. Thus, the result given in Eq. (2), along with the laws governing the scaling of Gaussian modes with changes in the resonator's dimensions, shows that for a given excitation laser power, Raman emission into the cavity mode is increased as the resonator length is decreased.

For fundamental Gaussian modes, the double resonance condition requires that:

$$\frac{mc}{2nL} - \frac{m'c}{2nL} = \Delta\nu_V \quad (3)$$

where $\Delta\nu_v$ is the Raman frequency, m and m' are integers and n is the refractive index of the sample (the same refractive index is assumed for both the laser and Raman shifted wavelengths, because they are generally very close to each other).

When the frequencies are expressed in terms of wavenumbers, Equation (3) may be written as $$\frac{\Delta m}{2nL} = \Delta\bar{\nu}_V \quad (4)$$

Thus it is seen that only a discrete set of cavity lengths are permitted for any given Raman transition. These cavity lengths in turn dictate a discrete set of permissible excitation laser wavelengths.

Figure 1:
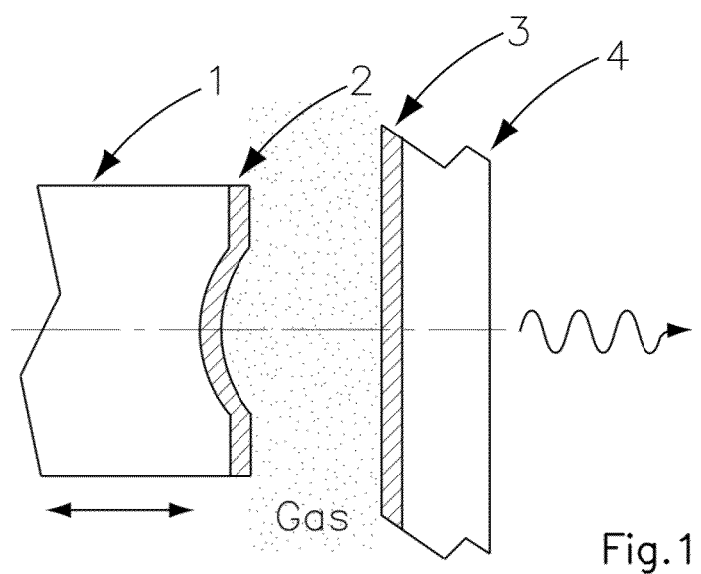
FIG. 1 shows a preferred embodiment of the Fabry-Perot microcavity.

With reference to FIG. 1, in one embodiment the microcavity is comprised of a concave reflector 2 fabricated at the end of an optical fiber 1 and a flat (or slightly concave) reflector 3 deposited on a thin substrate 4. The concave reflector 2 conforms to a spherically shaped crater formed in a polished end of the optical fiber 1. This micro-indentation feature can be created, for example, by the process of ablation with the use of one or more pulses of a focused beam from a $CO_2$ laser. The reflectors 2 and 3 can be produced, for example, by ion beam sputtering, which is known to be capable of yielding coatings with extremely high reflectivities. The sample from which Raman emission is sought is made to fill the space between mirrors 2 and 3. For maximum enhancement of the Raman emission from the sample, the reflectivities of the mirrors should be made as large as possible at both the wavelength of the excitation laser and the wavelength of the Raman emission.

In a preferred embodiment, the reflector 3 is kept in a fixed position while the reflector 2 is constrained to be translatable only in the direction parallel to the fiber axis. The excitation laser beam is made incident into the microcavity from the right in FIG. 1. Raman emission from the sample is coupled out of the microcavity through the reflector 3.

Figure 2:
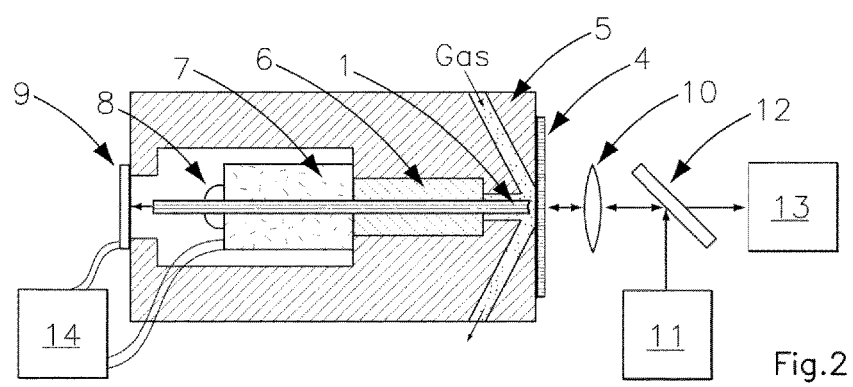
FIG. 2 is a schematic for the doubly resonant microcavity Raman sensor.

A schematic illustrating the overall Raman sensor is shown in FIG. 2. Output from a stabilized laser 11, tuned to the appropriate excitation wavelength, is made incident on a dichroic reflector 12, which is highly reflective at the excitation wavelength and highly transmitting at the Raman emission wavelength. The laser light from the stabilized laser 11 is then mode matched into the microcavity 5 with the use of lens 10. The optical fiber 1 is inserted into a close fitting ferrule 6 which permits free translation in the direction parallel to the fiber's optic axis. At the other end of the ferrule 6 the fiber is attached to a piezoelectric transducer 7 with the use of adhesive 8. The laser light exiting the fiber is made incident on detector 9. The output from the detector 9 is used to keep the microcavity always resonant with the excitation laser wavelength through the use of feedback electronics 14. The piezoelectric transducer 7 may adjust the cavity length (i.e. separation between the reflectors 2, 3) as necessary for initial set-up as well as during subsequent operation of the sensor to compensate for any dimensional changes due to temperature variations. The Raman emission coupled out of the flat reflector positioned on the substrate 4 of the microcavity is collimated by lens 10, passed through the dichroic filter 12, and made incident on detector 13. Once the system has been calibrated, the Raman signal measured by detector 13 will give directly the concentration of the species of interest which produces the Raman emission.

The capability of the doubly resonant microcavity Raman sensor will now be illustrated in the context of its application to the measurement of atmospheric $CO_2$ concentration. Suppose the 1,388 $cm^{-1}$ Raman transition in $CO_2$ is to be employed and the microcavity is semi-confocal. Then one possible cavity length is 25 μm (for $\Delta m=7$), and one possible excitation laser wavelength is 640 nm (for m=78), with a corresponding Raman emission wavelength of 702 nm. The differential Raman cross section for the 1,388 $cm^{-1}$ transition for 640 nm excitation is approximately $2(10)^{-31}$ $cm^2/sr$.

Suppose further that a laser power of 100 mW is available and that the microcavity mirrors have a reflectivity of 99.99% at both 640 nm and 702 nm. At a typical atmospheric $CO_2$ concentration of 400 ppm and for an expected Raman linewidth of around 2 GHz, one calculates a Raman emission rate through mirror 3 of $5(10)^5$ photons/s with the use of Eq. (2). If the detector 13 is a single photon counter and a measurement time of 10 s is employed, then a shot noise of approximately $2(10)^3$ counts can be expected. This implies that changes in the $CO_2$ concentration of about 0.2 ppm (i.e. 0.05% relative change) should be detectable with a response time of 10 s.

It will thus be seen that the objects set forth above, and those made apparent from the foregoing disclosure, are efficiently attained and since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A Raman sensor for detecting the concentration of a species of interest in a sample, the sensor comprising:
   a first substantially flat reflector;
   an adjustable optical fiber, wherein the adjustable optical fiber is translatable in a direction parallel to the fiber optic axis of the optical fiber;
   a second substantially concave reflector positioned at a proximate end of the optical fiber and aligned substantially normally to the first reflector, the second reflector separated from the first reflector by a distance to form a microcavity having a microcavity length equal to the distance between the first reflector and the second reflector, wherein the microcavity length is dependent upon the Raman transition of a species of interest to be detected;
   an excitation laser positioned to emit at an excitation wavelength incident upon the first reflector and the second reflector, wherein the wavelength of the excitation laser is dependent upon the microcavity length between the first reflector and the second reflector; and
   a Raman emission signal detector positioned to receive the Raman emission coupled out of the first reflector and to detect the concentration of the species of interest within a sample positioned between the first reflector and the second reflector.

2. The sensor of claim 1, wherein the microcavity is a Fabry-Perot microcavity.

3. The sensor of claim 1, wherein the microcavity length is approximately less than 1 mm.

4. The sensor of claim 1, wherein the first substantially flat reflector is fabricated on a substantially planar substrate.

5. The sensor of claim 1, wherein the second substantially concave reflector conforms to a spherically shaped depression formed within a polished end of the optical fiber.

6. The sensor of claim 1, further comprising a close fitting ferrule, the optical fiber positioned within the close fitting ferrule to constrain the optical fiber to allow translation of the optical fiber in the direction parallel to the fiber's optic axis.

7. The sensor of claim 1, further comprising a piezoelectric transducer coupled to a distal end of the optical fiber, the piezoelectric transducer to adjust the length of the microcavity by translating the optical fiber in the direction parallel to the fiber's optic axis.

8. The sensor of claim 6, further comprising:
   an excitation light detector positioned at a distance from the distal end of the optical fiber;
   a feedback module coupled to the excitation light detector and to the piezoelectric transducer, the excitation light detector to receive emissions from the distal end of the optical fiber and to adjust the length of the microcavity through the feedback module.

9. The sensor of claim 1, further comprising a dichroic filter positioned between the excitation laser and the first reflector, the diachronic filter having high reflectance at the wavelength of the excitation laser and high transmittance at the Raman emission wavelength.

10. The sensor of claim 1, further comprising a lens positioned between the first reflector and the dichroic filter, the lens to mode match the laser beam into the microcavity and to collimate the Raman emission coupled out of the first reflector onto the Raman emission signal detector.

11. The sensor of claim 1, wherein the first substantially flat reflector exhibits a high reflectivity at the excitation laser wavelength and at the Raman emission wavelength.

12. The sensor of claim 1, wherein the second substantially concave reflector exhibits a high reflectivity at the excitation laser wavelength and at the Raman emission wavelength.

13. The sensor of claim 1, wherein the sample is a liquid.

14. The sensor of claim 1, wherein the Raman emission signal detector is a single photon counter.

15. A Raman sensor for detecting the concentration of a species of interest in a sample, the sensor comprising:
   a first substantially flat reflector;
   an adjustable optical fiber, wherein the adjustable optical fiber is translatable in a direction parallel to the fiber optic axis of the optical fiber;
   a second substantially concave reflector positioned at a proximate end of the optical fiber and aligned substantially normally to the first reflector, the second reflector separated from the first reflector by a distance to form a microcavity having a microcavity length equal to the distance between the first reflector and the second reflector, wherein the microcavity length is dependent upon the Raman transition of a species of interest to be detected;
   an excitation laser positioned to emit an excitation wavelength incident upon the first reflector and the second reflector, wherein the wavelength of the excitation laser is dependent upon the microcavity length between the first reflector and the second reflector;
   a dichroic filter positioned between the excitation laser and the first reflector, the dichroic filter having high reflectance at the wavelength of the excitation laser and high transmittance at the Raman emission wavelength;
   a lens positioned between the first reflector and the dichroic filter, the lens to mode match the laser beam into the microcavity and to collimate the Raman emission coupled out of the first reflector onto the Raman emission signal detector;
   a close fitting ferrule, the optical fiber positioned within the close fitting ferrule to constrain the optical fiber to allow translation of the optical fiber in the direction parallel to the fiber's optic axis;
   a piezoelectric transducer coupled to a distal end of the optical fiber, the piezoelectric transducer to adjust the length of the microcavity by translating the optical fiber in the direction parallel to the fiber's optic axis;
   an excitation light detector positioned at a distance from the distal end of the optical fiber;
   a feedback module coupled to the excitation light detector and to the piezoelectric transducer, the excitation light detector to receive emissions from the distal end of the optical fiber and to adjust the length of the microcavity through the feedback module; and
   a Raman emission signal detector positioned to receive the Raman emission coupled out of the first reflector and to detect the concentration of the species of interest within a sample positioned between the first reflector and the second reflector.

16. A method for detecting the concentration of a species of interest within a sample using Raman emission, the method comprising:
   introducing a sample into a microcavity, the microcavity formed by a first substantially flat fixed reflector separated from a second substantially concave reflector positioned at a proximate end of a translatable optical fiber by a microcavity length, wherein the microcavity length is dependent upon the Raman transition of a species of interest to be detected in the sample;

introducing an excitation laser beam into the microcavity to establish a double resonance condition within the microcavity, wherein an excitation wavelength of the excitation laser beam is dependent upon the microcavity length between the first reflector and the second reflector; and detecting a Raman emission signal coupled out of the first reflector to determine the concentration of the species of interest within the sample.

17. The method of claim 15, further comprising translating the optical fiber in a direction parallel to a fiber optic axis of the optical fiber to adjust the microcavity length.

18. The method of claim 16, wherein translating the optical fiber in a direction parallel to a fiber optic axis of the optical fiber to adjust the microcavity length further comprises:

detecting an emission signal from a distal end of the optical fiber; and adjusting the microcavity length based upon the measured emission signal.

19. The method of claim 15, wherein introducing an excitation laser beam into the microcavity further comprises, reflecting the excitation beam off of a dichroic filter, the dichroic filter a having high reflectance at the wavelength of the excitation laser and high transmittance at the Raman emission wavelength.

20. The method of claim 15, wherein detecting a Raman emission signal further comprises, collimating the Raman emission signal coupled out of the first reflector onto a Raman emission signal detector.

21. The method of claim 15, wherein the sample is a liquid.

\* \* \* \* \*